US012806022B2

(12) United States Patent
Higgs, III et al.

(10) Patent No.: US 12,806,022 B2
(45) Date of Patent: Nov. 24, 2026

(54) MACHINE LEARNING ENABLED MODEL TO OPTIMIZE DESIGN OF OSSEOINTEGRATION-FRIENDLY PATIENT SPECIFIC 3D PRINTED ORTHOPEDIC IMPLANTS

(71) Applicant: William Marsh Rice University, Houston, TX (US)

(72) Inventors: C. Fred Higgs, III, Houston, TX (US); Prathamesh S. Desai, Houston, TX (US); Olufunto Faweya, Houston, TX (US); Benjamin J. Fregly, Houston, TX (US); Ata Babazadeh Naseri, Houston, TX (US)

(73) Assignee: William Marsh Rice University, Houston, TX (US)

( * ) Notice: Subject to any disclaimer, the term of this patent is extended or adjusted under 35 U.S.C. 154(b) by 955 days.

(21) Appl. No.: 18/001,678

(22) PCT Filed: Jun. 14, 2021

(86) PCT No.: PCT/US2021/037217

§ 371 (c)(1),
(2) Date: Dec. 13, 2022

(87) PCT Pub. No.: WO2021/257449

PCT Pub. Date: Dec. 23, 2021

(65) Prior Publication Data

US 2023/0225871 A1 Jul. 20, 2023

Related U.S. Application Data

(60) Provisional application No. 63/038,888, filed on Jun. 14, 2020.

(51) Int. Cl.
*A61F 2/30* (2006.01)
*A61F 2/32* (2006.01)
*A61F 2/36* (2006.01)

(52) U.S. Cl.
CPC ........ *A61F 2/3094* (2013.01); *A61F 2/30767* (2013.01); *A61F 2002/30011* (2013.01)

(58) Field of Classification Search
None
See application file for complete search history.

(56) References Cited

U.S. PATENT DOCUMENTS 9,034,048 B2 * 5/2015 Choren ................ A61F 2/3662 623/18.11
10,279,521 B1 * 5/2019 Pawar .................... B33Y 80/00
(Continued)

FOREIGN PATENT DOCUMENTS

JP 2023510745 A * 3/2023 ............. A61B 34/25
WO WO-2013091085 A1 * 6/2013 ............. A61L 27/56
(Continued)

OTHER PUBLICATIONS

International Search Report issued in International Application No. PCT/US2021/037217 dated Oct. 1, 2021 (3 pages).
(Continued)

*Primary Examiner* — Ann Hu
(74) *Attorney, Agent, or Firm* — Osha Bergman Watanabe & Burton LLP

(57) ABSTRACT

A method is disclosed for creating a patient-specific orthopedic implant. The method includes creating a numerical representation of an orthopedic implant design based on patient data describing an anatomical, physiological and pathological condition of a patient and simulating a characteristic of the orthopedic implant design based on the numerical representation. The method further includes
(Continued)

selecting a patient-specific orthopedic implant design based on the simulated characteristic of the orthopedic implant design and the patient data and constructing at least one patient-specific orthopedic implant based on the selected patient-specific orthopedic implant design.

18 Claims, 10 Drawing Sheets

(56) References Cited

U.S. PATENT DOCUMENTS

| | | | | |
|---|---|---|---|---|
| 10,799,363 | B2 * | 10/2020 | Pasini | A61C 13/0004 |
| 2002/0143268 | A1 * | 10/2002 | Meredith | A61B 5/1111 600/552 |
| 2009/0299173 | A1 * | 12/2009 | Cawley | A61B 5/0051 73/579 |
| 2012/0191200 | A1 | 7/2012 | Choren | |
| 2012/0329010 | A1 * | 12/2012 | Laster | A61C 8/0018 433/174 |
| 2014/0072929 | A1 * | 3/2014 | Cawley | G01N 33/4833 433/173 |
| 2015/0104755 | A1 * | 4/2015 | Laster | A61C 8/0022 433/174 |
| 2015/0230889 | A1 * | 8/2015 | Kim | A61C 8/0013 433/174 |
| 2020/0008848 | A1 * | 1/2020 | Hale | A61B 17/8071 |

FOREIGN PATENT DOCUMENTS

| | | | | |
|---|---|---|---|---|
| WO | WO-2014147566 | A1 * | 9/2014 | A61B 6/12 |
| WO | WO-2017151674 | A1 * | 9/2017 | A61P 19/02 |
| WO | WO-2021239932 | A1 * | 12/2021 | A61F 2/30756 |

OTHER PUBLICATIONS

Written Opinion issued in International Application No. PCT/US2021/037217 dated Oct. 1, 2021 (6 pages).

* cited by examiner

MACHINE LEARNING ENABLED MODEL TO OPTIMIZE DESIGN OF OSSEOINTEGRATION-FRIENDLY PATIENT SPECIFIC 3D PRINTED ORTHOPEDIC IMPLANTS

BACKGROUND

Patient-specific orthopedic implants used to replace large bone defects caused by cancerous bone tumors, or from local invasion of an organ cancer, or to replace bone affected by osteoporosis, or to replace bone traumatized/crushed due to an accident are yet to be perfected to have maximum lifetime and minimum rejection by the host body. The rejection of the implant by the host body can be either due to insufficient bone in-growth ("osseointegration"), stress-shielding (i.e., the mismatch of the elastic modulus of patient's bone and the implant material) or due to toxicity induced by the particles worn off from the implant over time. Osseointegration may be defined as a direct structural and functional connection between ordered, living bone and the surface of a load-carrying orthopedic implant. Factors such as implant biocompatibility, surface roughness, porosity, and loading conditions can influence the outcome of an orthopedic implant procedure. Imperfect osseointegration may result in problems such as mechanical failure, aseptic loosening, and infection. Revision surgery is often required to correct these implant failures.

Traditionally, bone implants have been fabricated with the one-size-fits-all outlook, owing to the limited manufacturing freedom previously offered by the molding and casting techniques. These over or under sized implants can be traumatic to the host body and can also result in rejection by the host body.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a method for creating a patient-specific orthopedic implant. The method includes creating a numerical representation of an orthopedic implant design based on patient data describing an anatomical, physiological and pathological condition of a patient and simulating a characteristic of the orthopedic implant design based on the numerical representation. The method further includes selecting a patient-specific orthopedic implant design based on the simulated characteristic of the orthopedic implant design and the patient data and constructing at least one patient-specific orthopedic implant based on the selected patient-specific orthopedic implant design.

In general, in one aspect, embodiments disclosed herein relate to a patient-specific orthopedic implant constructed, at least in part, from an architected material, wherein the anisotropic elastic moduli of the architected material matches the anisotropic elastic moduli of the patients health bone, thus minimizing the occurrence of stress-shielding by the orthopedic implant. Further, the unit lattice cells and meso-lattice cells from which the architected material is composed are designed to promote the rapid development of osseointegration. The patient-specific orthopedic implant may be formed by creating a numerical representation of an orthopedic implant design based on patient data describing the anisotropic elastic moduli and physiology of the patient's bone. Further, the forming may include simulating the elastic the anisotropic elastic moduli and osseointegration characteristics of the numerically represented design and selecting a patient-specific orthopedic implant design based on the similarity of the anisotropic elastic moduli and osseointegration characteristics of the design to those of the patient's healthy bone. Further, the forming may include constructing at least one patient-specific orthopedic implant based on the selected patient-specific orthopedic implant design.

In general, in one aspect, embodiments disclosed herein relate to a non-transitory computer readable medium storing instructions executable by a computer processor, the instructions including functionality for creating a numerical representation of an orthopedic implant design based on patient data describing an anatomical, physiological and pathological condition of a patient. The instructions further including functionality for simulating a characteristic of the orthopedic implant design based on the numerical representation and selecting a patient-specific orthopedic implant design based on the simulated characteristic of the orthopedic implant design and the data from the patient.

In general, in one aspect, embodiments disclosed herein relate to a system for creating a patient-specific orthopedic implant, including an additive manufacturing machine; and a computer processor. The computer processor configured to create a numerical representation of an orthopedic implant design based on the patient data describing an anatomical, physiological and pathological condition of a patient, and simulate a characteristic of the orthopedic implant design based on the numerical representation. The computer processor is further configured to select a patient-specific orthopedic implant design based on the simulated characteristic of the orthopedic implant design and the patient data, and three-dimensionally (3D) print the patient-specific orthopedic implant using an additive manufacturing technique using the selected patient-specific orthopedic implant design.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms “before”, “after”, “single”, and other such terminology. Rather, the use of ordinal numbers is to distinguish between the elements. By way of an example, a first element is distinct from a second element, and the first element may encompass more than one element and succeed (or precede) the second element in an ordering of elements.

Embodiments disclosed herein relate to methods and systems to design and manufacture an orthopedic implant tailored to an individual patient. Such patient-specific orthopedic implants can maximize the therapeutic lifetime of the implant by minimizing wear and fatigue-based failure, while reducing patient recovery time by facilitating speedy osseointegration and matching the mechanical properties of the implant as closely as possible to those of the patient’s healthy bone. The design component of orthopedic implant includes computational simulation of the mechanical, fluid flow, and osseointegration properties of the orthopedic implant. The manufacture design component of the orthopedic implant includes the use of additive manufacturing techniques to form the orthopedic implant in part or in full.

Orthopedic patients may require orthopedic implants to treat bone defects resulting from a number of causes. These causes may include, without limitation, cancerous bone tumors, local invasion into the bone of an organ cancer, replacement of bone affected by osteoporosis, replacement of joints damaged by osteoarthritis, rheumatoid arthritis, traumatic arthritis and replacement of bone traumatized by accident or injury.

Figure 1:
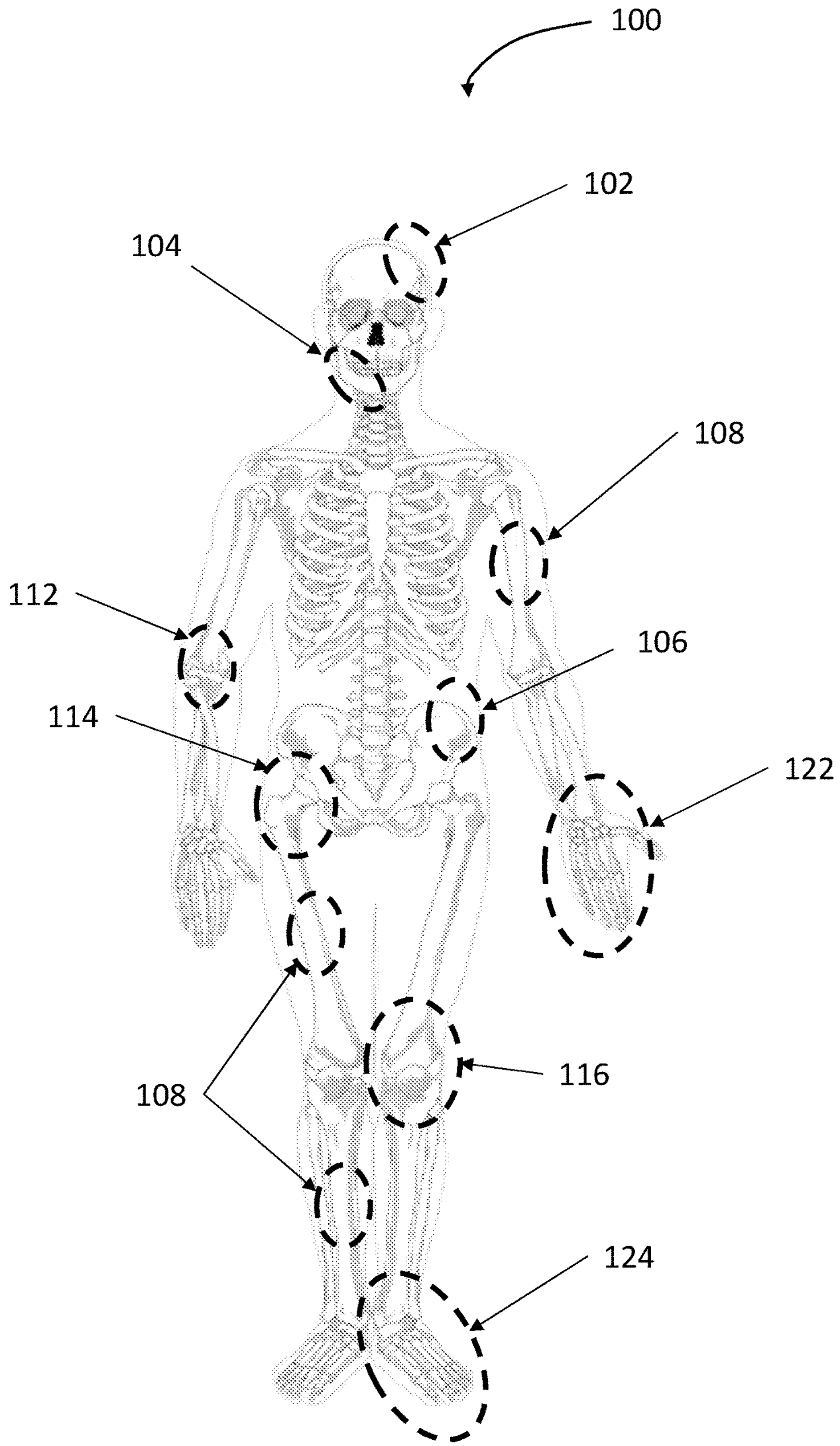
FIG. 1 depicts a human skeleton in accordance with one or more embodiments.

FIG. 1 depicts a human skeleton (100) and some example locations at which orthopedic implants are commonly required. Locations include the skull (102), craniofacial bone (104), pelvis (106), major bones of the limbs (108), as well as the elbow (112), hip (114) and knee (116) joints, or smaller bones in the wrist and hand (122) or ankle and foot (124). The characteristics of healthy bones, such as bone strength, elasticity, density, and resistance to wear or fatigue-based failure, may differ from one location to another within a single patient. In addition, healthy bone characteristics may differ between patients in both a stochastic manner and systematically based on factors such as age, gender, ethnic background, and nutritional and disease history.

Ideally, the characteristics of an orthopedic implant, including strength, elasticity, density, and resistance to wear or fatigue-based failure, as well as the geometry and macro-dimensions of the implant, should closely match the characteristics of the adjacent healthy bone to which the implant is joined. However, present orthopedic implant designs are limited by material, casting and molding constraints and are based on expensive and time consuming in-vitro or in-vivo testing. Such methods are ill suited to a patient-specific orthopedic implant design approach and instead the patient and surgeon are frequently required to choose between a small number of options or have no choices at all.

For example, it is important that the elasticity of the orthopedic implant and that of the surrounding healthy bone match well to prevent stress-concentration and stress-shielding that if present may lead to premature failure of the implant. The elasticity of healthy bone may be anisotropic, meaning it is more resistant to deformation (strain) when subject to stress applied along one axis, than to stress applied along a second, orthogonal, axis. Bone may be categorized as compact or dense surface bone, referred to as cortical bone, and porous sub-surface bone referred to as cancellous bone. The cortical bone is transversely isotropic, i.e., isotropic in the longitudinal direction and isotropic in radial and circumferential directions but not in all the directions. Human long bones may have a significant anisotropy in mesoscale. On the other hand, cancellous bone is made up of trabeculae, i.e., thin struts or plates, and may exhibit either perfect isotropy or perfect anisotropy depending on the bone’s location. If the cancellous bone material is located in the core of the bone, then it may be substantially isotropic. If it is located adjacent to the cortical bone it may be anisotropic.

Optimally, an orthopedic implant sharing an interface with the cancellous bone should be designed so that the orthopedic implant and the healthy bone react similarly to imposed stress. If the implant bears most or all the load because of its greater stiffness without transferring it to the cancellous bone in which it is fixed, then the body may reabsorb portions of the unused cancellous bone. This phenomenon, that may result in loosening of the implant, is referred to as bone resorption due to stress-shielding. In stress-shielding the host cancellous bone is ‘shielded’ by the implant from the stress borne by the skeleton. Besides matching Young’s modulus of the native bone, adapting to the anisotropy of the bone is a critical factor in designing biomimetic bone substitutes, particularly orthopedic implants.

Mathematically, anisotropic elasticity may be represented in a Cartesian coordinate system by a fourth-order elastic stiffness tensor, $c_{ijkl}$, that relates the strain, $\varepsilon_{kl}$ to the stress, $\tau_{ij}$ to:

$$\tau_{ij}=c_{ijkl}\varepsilon_{kl} \qquad \text{Equation (1)}$$

where each of the indices i, j, k, and l can take the values 1, 2, and 3 enumerating the orthogonal Cartesian axis, and the Einstein summation convention applies for repeated indices. In general, $c_{ijkl}$, may have 21 independent elastic moduli and ideally the elastic moduli of the implant and the elastic moduli of the surrounding healthy bone should be closely matched to prevent stress-concentration and stress-shielding effects.

In accordance with one or more embodiments, a sample of healthy bone may be taken from a suitable location within the patient. For example, a suitable sample location may be bone adjacent to the transplant site. Alternatively, a suitable sample location may be an anatomically similar site. For example, if the orthopedic implant site is in the left femur, then an anatomically similar sample site may be the right femur. At least one elastic moduli of the sample of healthy bone may then be measured, in accordance with one or more embodiments. The measurement may be made by utilizing a uniaxial press or triaxial press using protocols familiar to one of ordinary skill in the art. In accordance with one or more embodiments, materials with elastic moduli to match those of the healthy bone samples from the patient may then be designed and manufactured using the methods and systems disclosed below.

In accordance with other embodiments, healthy bone characteristics may be determined by remote sensing techniques. For example, bone density may be determined using dual-energy x-ray absorptionmetry. Other remote sensing methods for characterizing healthy and diseased bone, including CT scans, PET scans, MRI scans, and nuclear bone scans are well known to a person of ordinary skill in the art.

Figure 2A:
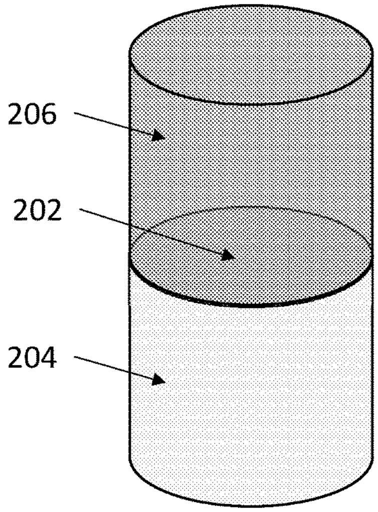
FIGS. 2A-2C depict in-growth of healthy bone into implant materials in accordance with one or more embodiments.

In addition, to matching the elastic moduli of the surrounding healthy bone, an ideal orthopedic implant design will promote the in-growth of the surrounding healthy bone into the matrix of the orthopedic implant surface, thus minimizing the time over which additional support in the form of orthopedic screws and plates or other means of rigidly connecting the implant and the surrounding bone is required. FIG. 2A depicts the interface (202) between a segment of healthy bone (206) and a segment of orthopedic implant composed of a solid material (204). If the solid material (204) of the orthopedic implant has no porosity, at scales greater than the molecular level, the amount of in-growth of the bone into the material of the implant will be minimal. Finishing the surface of the orthopedic implant with a rough surface may improve the long-term adhesion between the healthy bone and the orthopedic implant somewhat but the result may be less than optimal.

Figure 2B:
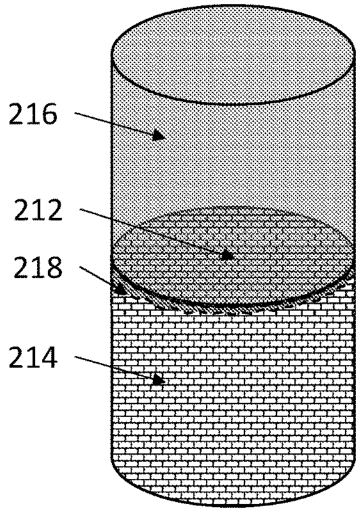

FIG. 2B depicts the interface (212) between a segment of healthy bone (216) and a segment of orthopedic implant composed of a porous material (214). The porous material (214) of the orthopedic implant has voids (pores) within the porous material (214) for the bone to grow into, but if the pores are not interconnected, i.e., if the porous material (214) has little or no permeability, then the osteoblast, the main cells of bone formation responsible for the synthesis, secretion, and mineralization of bone matrix, that are the precursor to bone growth may not penetrate far into the porous material and the thickness of the region of in-growth (218) may be small.

Figure 2C:
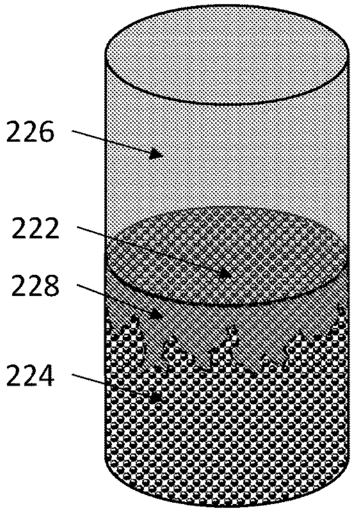

In contrast, in accordance with one or more embodiments, FIG. 2C depicts an interface (222) between a segment of healthy bone (226) and a segment of orthopedic implant composed of a porous and permeable material (224). The porous and permeable material (224) of the orthopedic implant has both voids (pores) for the bone to grow into, and interconnected passageways that may permit the osteoblasts to enter. Thus, for a porous and permeable material the thickness of the region of osseointegration (228) into the orthopedic implant may be large, promoting a stronger attachment and long-term fixation between the orthopedic implant and the surrounding healthy bone.

In accordance with one or more embodiments, a porous and permeable architected material may be formed by constructing a three-dimensional (3D) lattice of interconnected unit lattice cells (302). The architected material may be formed from a plurality of unit lattice cells arranged in contact with one another.

Figure 3A:
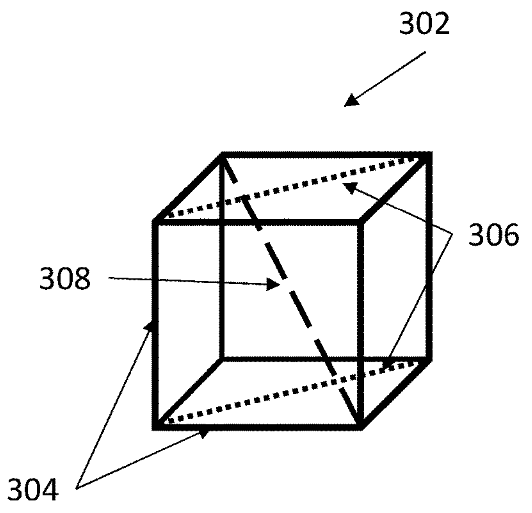
FIGS. 3A-3D shows a plurality of lattice cells in accordance with one or more embodiments.

A cubic unit lattice cell is depicted in FIG. 3A. Each unit lattice cell may include a plurality of struts (304) arranged in a variety of geometries. The struts (304) may form the edges of the unit lattice cell (302) or may form face-diagonal strut (306) cross-bracing the face of the unit lattice cell (302), or body-diagonal struts (308) cross-bracing the volume of the unit lattice cell (302). The unit lattice cell (302) may be cubic, as shown in FIG. 3A. Alternatively, the unit lattice cell (302) may be octahedral, dodecahedral, icosahedral, or any one of many other types of unit lattice cell well known to a person of ordinary skill in the art.

Figure 3B:
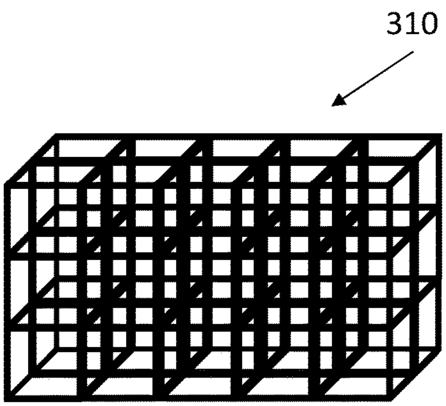

In accordance with one or more embodiments, a plurality of unit lattice cells (302) may be combined to form an architected material (310), as shown in FIG. 3B. The architected material (310) may form an orthopedic implant in its entirety, or the architected material (310) may form a portion of an orthopedic implant.

Figure 3C:
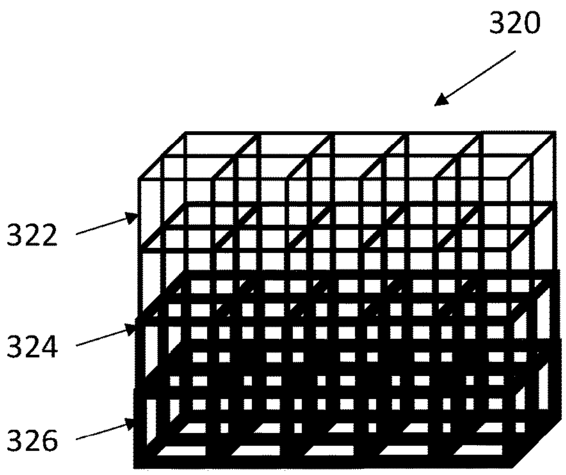

In some embodiments a plurality of unit lattice cell (302) of a single design may be combined to form an architected material. In other embodiments, a plurality of unit lattice cells (302) of a plurality of designs may be combined to form the architected material. FIG. 3C depicts an example where unit lattice cells (302) have been combined to form a heterogeneous material (320). In FIG. 3C the unit cells near the top of the portion of architected material (322) have thin struts, while the unit cells near the bottom of the portion of architected material (326) have thick struts, and the unit cells near the center of the portion of architected material (324) have struts of an intermediate material. In accordance with one or more embodiments, the porosity near the top of the portion of architected material (322) may be higher than the porosity near the bottom of the portion of architected material (326). Conversely, the mechanical strength near the top of the portion of architected material (322) may be lower than the porosity near the bottom of the portion of architected material (326), assuming the material from which the struts (304, 306, 308) are made is common to the top portion and the bottom portion.

Figure 3D:
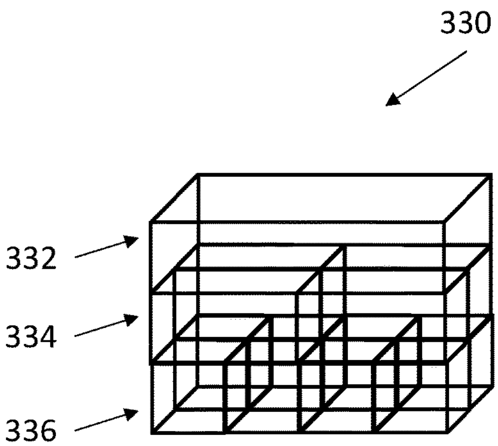

FIG. 3D depicts an architected material (330) where the size of the unit lattice cell (302) decreases between the top (332) and the middle (334), and decreases still further between the middle (334) and the bottom (336) of the portion of architected material (330). Consequently, if the material from which the struts (304, 306, 308) are made is common to all portions of the architected material (330) the porosity may decrease between the top (332) and the middle (334), and decreases still further between the middle (334) and the bottom (336) of the portion of architected material (330). Conversely, the mechanical strength near the top of the portion of architected material (332) may be lower than the porosity near the bottom of the portion of architected material (336), assuming the material from which the struts (304, 306, 308) are made is common to the top portion and the bottom portion.

All the examples depicted in FIGS. 3A-3D use cubic or rectangular cuboid unit lattice cells. In other embodiments (not shown) the unit lattice cell (302) may be octahedral, dodecahedral, icosahedral, or any one of many other types of unit lattice cell well known to a person of ordinary skill in the art, and the types may be used individually or in combination to form an architected material, without departing from the scope of the invention.

The elastic moduli, the density, and the porosity of each cell may depend on the orientation and geometry of the struts (304, 306, 308). The elastic moduli may further depend on the dimensions of each strut (304, 306, 308) including its length, cross-sectional area, and cross-sectional shape. The elastic moduli and the density of each cell may also depend on the material from which the struts (304, 306, 308) are fashioned. For example, a unit lattice cell (302)

having struts (304, 306, 308) composed of titanium may have different, stiffer, elastic moduli than a unit lattice cell with identical geometry having struts (304, 306, 308) composed of tri-calcium phosphate. Suitable materials for the struts (304, 306, 308) of the unit lattice cell may include, without limitation, β tri-calcium phosphate for non-skeletal joint locations, and titanium-64, tantalum, cobalt-chrome, and polyether ether ketone (PEEK) for skeletal joint locations.

The porosity and permeability of the architected material made up of a plurality of unit lattice cells (302) will also depend on the orientation and geometry of the struts (304, 306, 308), as well as the length, cross-sectional area and cross-sectional shape of the struts (304, 306, 308). In general, the less porous and permeability the architected material is, the stronger and more rigid it may be. However, for a given porosity and permeability there is a wide range of strength and elastic moduli that may be achieved using different unit lattice cell (302) designs.

In accordance with one or more embodiments, the architected material of the orthopedic implant may be composed of uniformly repeating unit lattice cells (302). In these embodiments, the material of the orthopedic implant, while heterogeneous on the scale of the unit lattice cell (302), is homogenous on a larger scale. In other embodiments, the unit lattice cells (302) may vary with position within the orthopedic implant. For example, unit lattice cells (302) with relatively high porosity and permeability may be used for the surface of the orthopedic implant intended to be in proximity with healthy bone, while unit lattice cells (302) with relatively low porosity and permeability but higher strength and rigidity may be used for core portions of the orthopedic implant.

In accordance with one or more embodiments, the transition from one type of unit lattice cell (302) to another may be a gradual transition over spatial position. In accordance with other embodiments, the transition between two or more types of unit lattice cell (302) may be a sharp transition at one or more interfaces.

In accordance with one or more embodiments, a set of directional cubic unit lattice cells (302) with face-diagonal struts (306) and body-diagonal struts (308) may be chosen to act as the building blocks of a hierarchical lattice structure. Each unit lattice cell (302) may consist of a primitive (or simple) cubic cell with one face-diagonal strut (306) per face (totaling six face-diagonals struts per primitive cell in total) and one body-diagonal strut (308).

For example, the length of each primitive cell may be 1.5 millimeters (mm) and struts with a circular cross-section with identical diameters may be used to construct each primitive cell. The strut diameter may be 0.3, 0.4, 0.5, or 0.6 mm producing a porosity of 77.6%, 63.6%, 48.4%, and 33.4%, respectively. The choice of the orientation of the body-diagonal strut (308) may define the orientation of the stiffest direction of the primitive cell. Face-diagonal strut (304) orientation may be selected so that the resulting primitive cell is centrosymmetric along the axis of the chosen body-diagonal strut (308). The sizes and dimensions described in this paragraph, and elsewhere, are intended to be illustrative examples only, and not to limit in any way the scope of the invention.

Figure 4:
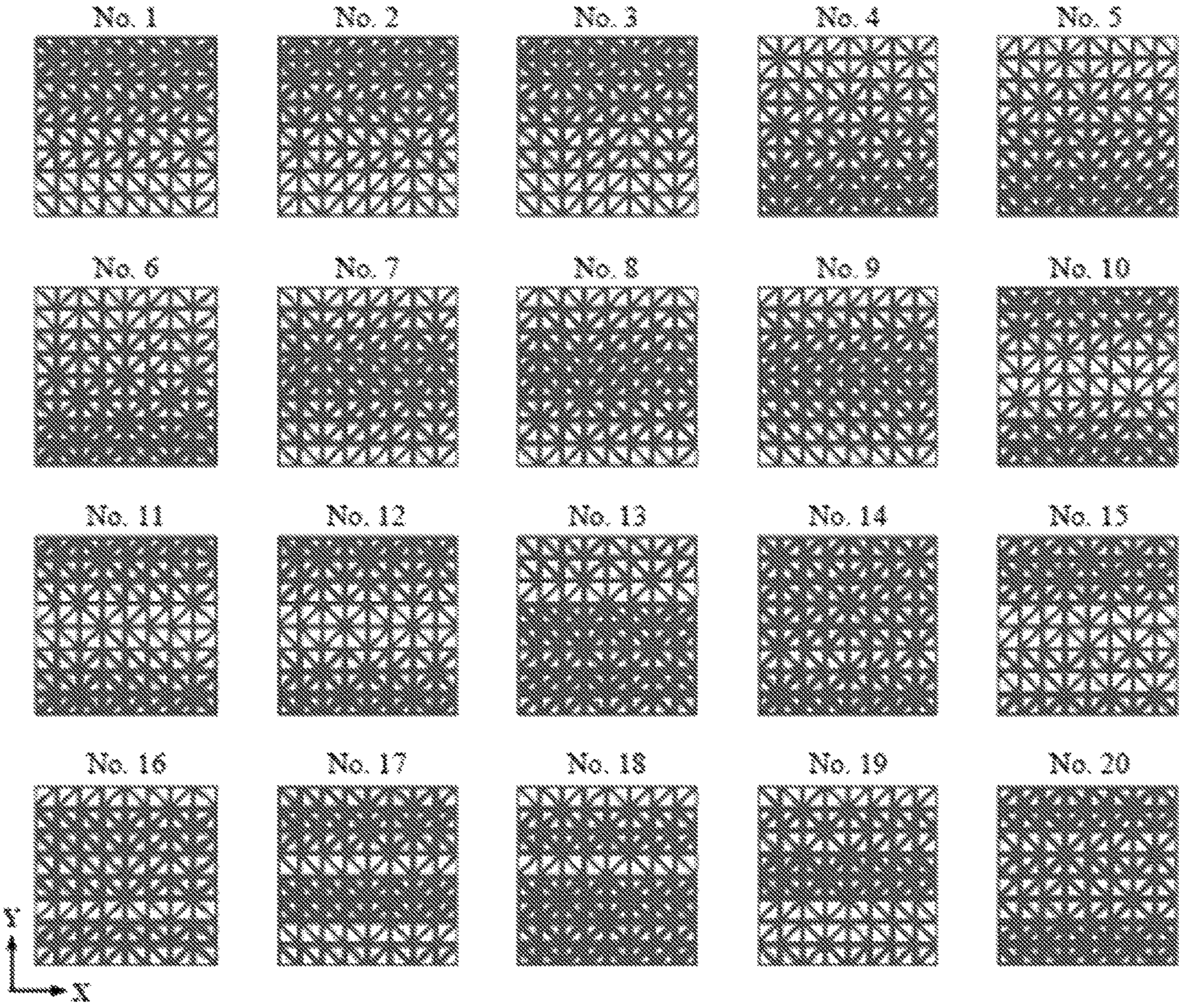
FIG. 4 depicts a cross-section through a plurality of meso-lattice cells in accordance with one or more embodiments.

In accordance with one or more embodiments, a hierarchical lattice structure design may be used. It may be convenient to determine a plurality of meso-lattice cell designs, with each meso-lattice cell design comprised of a plurality of unit lattice cells. Each meso-lattice cell consists of an assembly of the unit-lattice cells. The configuration of unit lattice cells within each meso-lattice cell may be selected to produce predetermined porosity, anisotropic elastic moduli, and osseointegration characteristics. FIG. 4 depicts a cross-section through 20 examples of meso-lattice cell designs, in accordance with one or more embodiments. In some embodiments more than 20 meso-lattice cell designs may be determined, and in other embodiments fewer than 20 meso-lattice cells designs may be determined.

A plurality of meso-lattice cells may be combined to form an architected material, with known porosity, anisotropic elastic moduli, and osseointegration characteristics. In some embodiments, each meso-lattice cell forming the plurality may have the same meso-lattice cell design creating a homogeneous architected material at a scale larger than the meso-lattice cell size. In other embodiments, the plurality of meso-lattice cells may be formed from a plurality of different meso-lattice cell design creating a heterogeneous architected material at a scale larger than the meso-lattice cell size.

In one or more embodiments, the orthopedic implants can be manufactured using an additive manufacturing machine. Many types of additive manufacturing machines are known to a person of ordinary skill in the art. For example, the additive manufacturing machine may be based upon powder bed fusion, material extrusion, stereolithography or digital light processing vat polymerization, masked stereolithography, selective laser sintering, material jetting, drop-on-demand, binder jetting, direct metal laser sintering, selective laser melting, and electron beam melting additive, without departing from the scope of embodiments herein.

Figure 5:
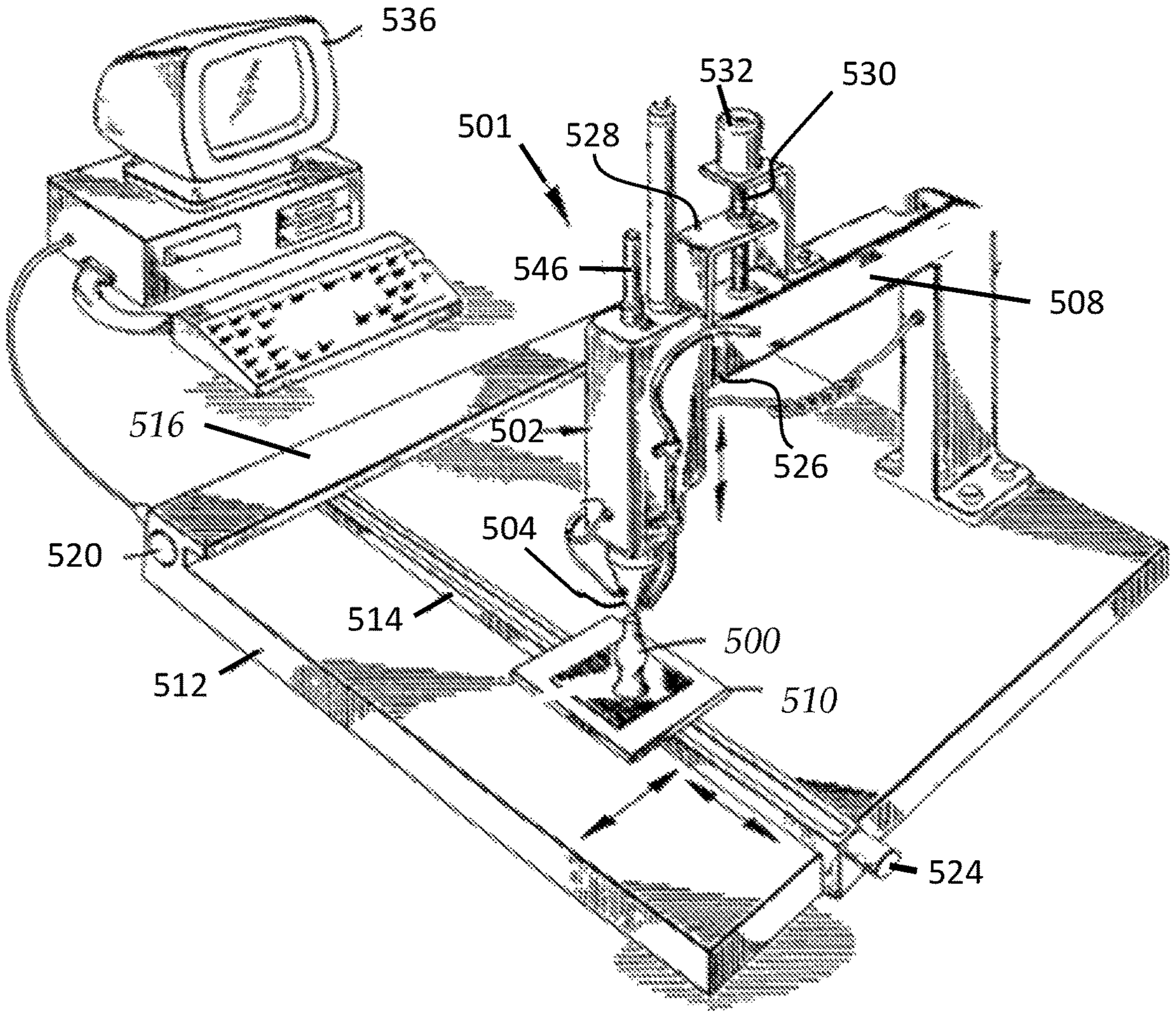
FIG. 5 shows an additive manufacturing machine in accordance with one or more embodiments.

FIG. 5 illustrates one embodiment of an additive manufacturing machine (501) for manufacturing an orthopedic implant (500), in accordance with one or more embodiments. The apparatus includes a movable dispensing head (502) having a discharge nozzle 404 at its bottom end, dispensing head (502) being supported from a pedestal (506) by a mounting arm (508). Dispensing head (502) is located close to a base member comprising a plate (510) on which the orthopedic implant (500) is to be formed.

Dispensing head (502) and base plate (510) are supported for mechanical movement relative to each other. This may be accomplished by providing mechanical means for translational movement of base plate (510), laterally along orthogonal axes of a horizontal base plane and for vertical movement of dispensing head (502). Accordingly, as is shown in FIG. 5, base plate (510) is supported on a horizontal table (512) having a sliding rod (514) in threaded engagement within its drive block (516) with a drive screw (not shown). Sliding rod (514) also carries an elongated drive screw (not shown) driven by a second motor (524) and coupled to mating threads (not shown) secured to the underside of base plate (510) for driving engagement therewith. Thus, the base plate (510) may be moved along the orthogonal horizontal axes indicated in FIG. 5 by the selected actuation of motors (524) and (520), respectively.

A separate mechanical drive provides for up and down vertical movement of the dispensing head (502). For that purpose, head (502) is mounted for vertical movement on a micro-slide bearing (526) on one end of support arm (508) by a bracket (528). One apertured end of right-angle bracket (528) is threadedly engaged with a drive screw (530). A third drive motor (532) supplies driving rotary power to screw (530) and is mounted on support arm (508) by bracket (534) as shown. Selected actuation of reversible motor (532) thus rotates screw (530) to provide up and down vertical movement of dispensing head (502) on slide bearing (526). For that purpose, motor (532) is preferably a high-resolution stepper motor. It is to be noted, however, that various types of motors can be used for drive motors (520), (524), and (532), including stepper motors, linear motors, servomotors, synchronous motors, D.C. motors, and fluid motors. Preferably, motors (520), (524), and (532) are computer-controlled by control signals transmitted from a computer (536), as discussed below.

Various materials in different forms may be used for manufacturing an orthopedic implant with the additive manufacturing described. For example, the material may be β tri-calcium phosphate, medical grade titanium alloys, Ti-6Al-4V (4V alloy), tantalum, cobalt-chrome, or PEEK. FIG. 5 illustrates an embodiment in which the working material is supplied in the form of a solid rod (546), heated to its melting point in dispensing head (502) and dispensed from nozzle (504) as a flowable fluid.

In accordance with one or more embodiments, the entire orthopedic implant may be printed in its final form ready for testing or clinical use. In these embodiments, the orthopedic implant may be printed with both the external macroscopic surface and the internal lattice structure executed by the additive manufacturing machine. In other embodiments, the orthopedic implant may require additional manufacturing steps after printing. For example, some portions of the surface of the orthopedic implant may require polishing, or grinding, or trimming. In other cases, solid metallic cores may need to be inserted into the portion of the orthopedic implant manufactured using additive manufacturing techniques.

In accordance with one or more embodiments, the manufacturing of the orthopedic implant may include coating the external macroscopic surface of the orthopedic implant with an osteoblast inducing substance. In accordance with other embodiments, the manufacturing of the orthopedic implant may include impregnating at least a portion of the material from which the orthopedic implant is composed with an osteoblast inducing substance. The impregnation may extend over a depth below the external macroscopic surface of the orthopedic implant. The distance may be half an inch [1.27 cm] or may be larger or small than half an inch [1.27 cm], according to one or more embodiments. The osteoblast inducing substance may promote the in-growth of the healthy bone into the orthopedic implant to increase the strength of the bond between the implant and the adjacent healthy bone and to minimize the patient's recovery time.

In accordance with one or more embodiments, the manufactured orthopedic implant may be tested prior to its therapeutic use. The testing may occur before or after the coating or impregnation of the orthopedic implant with an osteoblast inducing substance. The testing may occur if the coating or impregnation of the orthopedic implant with an osteoblast inducing substance is omitted from an embodiment. The protocol for testing the manufactured orthopedic implant may include manufacturing a single orthopedic implant and testing it before its therapeutic use. Alternative, the protocol may include manufacturing a set of two or more substantially similar orthopedic implants, selecting at least one of the substantially similar orthopedic implants for future therapeutic use, and conducting the testing on the remaining members of the set of substantially similar orthopedic implants.

The orthopedic implant may be tested to assess its characteristics. The characteristics may include, without limitation, elastic moduli, mechanical strength, susceptibility to wear and fatigue, and expected therapeutic lifetime before failure. Assessing the characteristics of the orthopedic implant may include determining if the value of one or more of its characteristic falls within a predetermined range. The predetermined range may be patient invariant or may be patient specific. For example, the predetermined range for the orthopedic implant's therapeutic lifetime may be 20 years or greater for any patient, or the threshold value may be equal to or greater than the patient's actuarial life expectancy.

In accordance with one or more embodiments, if one or more of the characteristics does not fall within the predetermined range the orthopedic implant may be redesigned. The purpose of the redesign may be to ensure that all the characteristics of the orthopedic implant fall within their predetermined range.

In accordance with one or more embodiments, computational modeling may be employed to design or redesign the orthopedic implant. The computational modeling may include simulation of the mechanical properties of the orthopedic implant. For example, the mechanical properties may include the porosity, elastic moduli, surface roughness, pore shape, resistance to wear, and resistance to fatigue-based failure. The computational modeling may include simulating fluid properties including permeability. The computational modeling may include simulating the in-growth of osteoblasts and new bone from the adjacent healthy bone into the orthopedic implant. The computational modeling may include the design of an architected material comprised of a plurality of unit lattice cells that may be manufactured using an additive manufacturing technique. Further, the computational modeling may simulate an additive manufacturing process, for example a powder bed fusion manufacturing process. If combined with additive manufacturing process models, the output of the computational modeling may include generating instructions to control an additive manufacturing machine to form one or more orthopedic implants.

In accordance with one or more embodiments, the computational model may utilize physics-based simulation algorithms. For example, the mechanical characteristics of the orthopedic implant may be simulated using a discrete element method (DEM), a finite element method (FEM), or a discrete Galerkin method (DGM). Similarly, computational fluid dynamics (CFD) methods including, without limitation a finite difference method (FDM), a finite volume method (FVM), a finite element method (FEM), a Lattice Boltzman Lattice Boltzmann Method (LBM), a spectral method, a smooth particle hydrodynamic (SPH) method, and other particle methods (e.g., molecular dynamics (MD), vortex, particle-in-cell methods, Direct Simulation Monte Carlo (DSMC), dissipative particle, etc.), may be used to simulate the flow of osteoblast inducing substances into the orthopedic implant. These CFD methods also includes machine learning-accelerated versions of these aforementioned CFD methods.

For example, continuum-based 3D FEM models may be used to represent the 3D geometry of the meso-lattice cell, alternatively, truss-based FEM models may be used. Results from simulations on unit lattice cells using the continuum-based 3D FEM models may be used to calibrate and verify truss-based FEM simulations allowing them to generate accurate results for meso-lattice cell modeling. Numerical homogenization techniques based on FEM may be applied to obtain the effective elastic moduli of a meso-lattice cell design, as the representative volume element (RVE) at a macro-scale. The effective macro-scale elastic stiffness tensor, $\bar{c}_{ijkl}$, may be calculated as:

$$\bar{\tau}_{ij} = \bar{c}_{ijkl}\bar{\varepsilon}_{kl} \quad \text{Equation (2)}$$

where $$\bar{\tau}_{ij} = \frac{1}{V_{RVE}} \int_{V_{RVE}} \tau_{ij} dV, \quad \text{Equation (3)}$$

$$\bar{\varepsilon}_{ij} = \frac{1}{V_{RVE}} \int_{V_{RVE}} \varepsilon_{ij} dV \quad \text{Equation (4)}$$

and $V_{RVE}$ is the volume of a representative volume element.

In accordance with one or more embodiments, rule-based computational modeling methods including cellular automata (CA) techniques may be used to predict the in-growth of bone from the adjacent healthy bone into the orthopedic implant. The rules required for rule-base computational modeling such as CA simulations may be determined based at least in part on a comparison of measured in-vitro experimental data and on simulated predictions of in-growth in the in-vitro experiments.

For example, agent-based modeling (ABM) is a discrete modeling technique based on the principles of cellular automata. ABM makes use of various "agents" whose time-evolution is governed by empirical rules. Even though simplistic at the agent level, these rules can simulate intricate systems with results exhibiting complicated temporal evolutions. According to one or more embodiments, common source software such as NetLogo may be used to perform ABM.

In accordance with one or more embodiments, cube-shaped agents representing solid implant parts, mesenchymal stem cells (MSCs), pre-osteoblast cells (OBp), and osteoblasts (OBa), may be used for osseointegration. Except for solid implant agents, these agents may be free to move inside the pores of the lattice. Empirical rules may simulate the motion of the agents and their subsequent differentiation from OBp to OBa. In accordance with one or more embodiments, cellular processes such as cell migration, cell proliferation, cell differentiation, and cell apoptosis may be probabilistically modeled. For example. cell migration simulation may involve the probabilistic movement of agents at a set migration rate by the distance of a single cubic element. Cell proliferation simulation may involve the probabilistic splitting of a single agent into two of the same type at a set proliferation rate. Cell differentiation simulation may involve the probabilistic evolution of an agent type into a more advanced agent type at a set differentiation rate, cell apoptosis simulation may involve the probabilistic death of an agent at a set apoptosis rate. The flow of growth factors and nutrients from the bone towards the lattice may be modeled by partial differential equations (PDEs), and the solution to the PDEs may be obtained using numerical methods involving iterative time-stepping algorithms.

In accordance with one or more embodiments, the unit lattice cell and meso-lattice cell designs that optimally match the patient's bone characteristics may be determined based on both the anisotropic elastic moduli and the osseointegration characteristics of the designs. The determination may be performed using an "osseointegration score" measuring the rate at which osseointegration proceeds after implanting the orthopedic implant into the patient, and a "stress-shielding prevention score" measuring the match between the elastic moduli or the orthopedic implant and the adjacent healthy bone of the patient. A good design for a patient-specific orthopedic implant will have both a high osseointegration score and a high stress-shielding prevention score.

For example, an osseointegration score may be determined based upon the volume fraction of the bone formation, i.e., the predicted ratio of bone volume to total volume (BV/TV) inside the porous implant after a period of time, such as 28 days, as predicted by the ABM of osseointegration. The volume of the bone tissue that grows inside the porous implant may be computed from the number of voxels occupied by $OB_p$ or $OB_a$ cells. The computed bone volume (BV) may be normalized by the total volume of the lattice (TV), including the pore volume and solid volume. The osseointegration performance ($PS_{BI}$) score of a lattice may be calculated as:

$$PS_{BI} = \frac{BV}{TV} = \frac{\sum(OB_p + OB_a)}{N_{vox}} \quad \text{Equation (5)}$$

where, $N_{vox}$ is the total number of voxels (or agents of the ABM) that fill the entire domain. Equation (5) is one example of a suitable $PS_{BI}$ but other definitions including, without limitation, using 21 days or 42 days for the period of time, or using the ratio of bone volume to pore volume, will be readily apparent to one of ordinary skill in the art.

Similarly, a stress-shielding prevention performance score ($PS_{SS}$) of a lattice design may be determine based on the volume, enclosed between the 3D surface representation of the anisotropic Young's modulus of the bone ($E_B$) and that of the anisotropic Young's modulus of the meso-lattice cell ($E_L$), normalized by the volume of $E_B$. $PS_{SS}$ may be defined as:

$$PS_{SS} = 1 - \frac{V_{LB}}{V_B} \quad \text{Equation (6)}$$

where $$V_B = \int\int\int_E E_B^2(\theta, \varphi)\sin\varphi d\varphi d\theta dE \quad \text{Equation (7)}$$

and $$V_{LB} = \int\int\int_E (E_L(\theta, \varphi) - E_B(\theta, \varphi))^2 \sin\varphi d\varphi d\theta dE. \quad \text{Equation (8)}$$

Equation (6) is one example of a suitable $PS_{SS}$ but other definitions will be readily apparent to one of ordinary skill in the art.

In accordance with one or more embodiments, a patient-specific orthopedic implant design may be selected by evaluating the stress-shielding prevention performance score, $PS_{SS}$, and osseointegration score, $PS_{BI}$ for a plurality of meso-lattice cell designs and selecting a design with both a high $PS_{SS}$ and a high $PS_{BI}$. The plurality of meso-lattice cell designs may be selected by randomly, or pseudo-randomly, combining different unit lattice cell designs, and by randomly, or pseudo-randomly, or deterministically varying the parameters, such as strut size, of the unit lattice cells, or by a combination of both.

Alternatively, an inversion technique may be used to find an optimum patient specific implant design. The inversion technique may include forming a cost function by combining the stress-shielding prevention performance score and osseointegration score and finding an extremum of the cost function using a conjugate-gradient optimization algorithm. A person of ordinary skill in the art will readily appreciate that many other inversion techniques may also be used for this purpose.

Further, in accordance with one or more embodiments, artificial intelligence (AI) techniques may be used to supplement or replace, partially or in full, at least one of the physics-based and the rule-based simulation techniques. For example, a stress-shielding prevention performance score and osseointegration score may be calculated for a small number of meso-lattice cells designs using the physics-based and the rule-based simulation techniques discussed previously. An artificial intelligence algorithm may be trained on the results of these simulations. The trained artificial intelligence algorithm may be used to predict new meso-lattice cell designs that may be used to manufacture orthopedic implants with elastic moduli and osseointegration characteristics that closely match those of the adjacent healthy patient bone.

Figure 6:
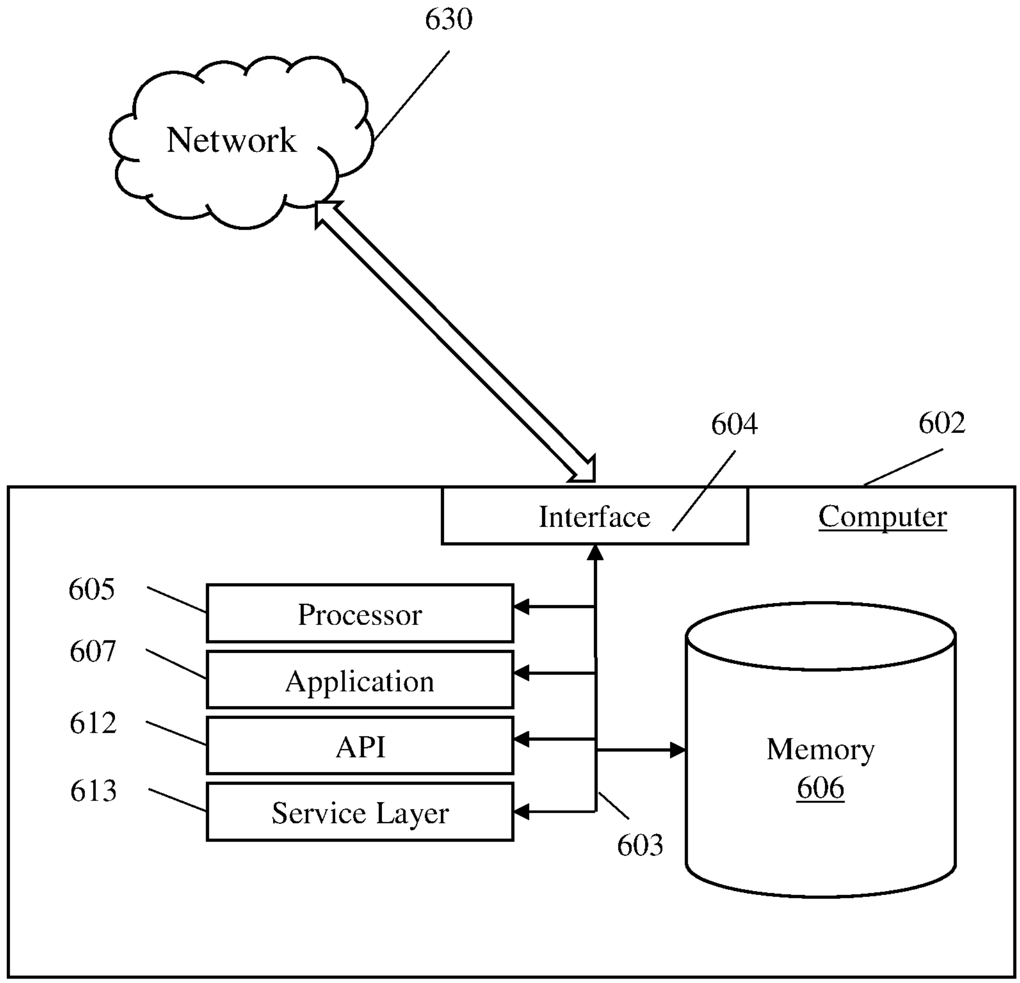
FIG. 6 shows a computer system in accordance with one or more embodiments.

FIG. 6 depicts a block diagram of a computer system (602) used to provide computational functionalities associated with described algorithms, methods, functions, processes, flows, and procedures as described in this disclosure, according to one or more embodiments. The illustrated computer (602) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (602) may include a computer that includes an input device, such as a keypad, keyboard, touch screen, or other device that can accept user information, and an output device that conveys information associated with the operation of the computer (602), including digital data, visual, or audio information (or a combination of information), or a graphical user interface (GUI).

The computer (602) can serve in a role as a client, network component, a server, a database or other persistency, or any other component (or a combination of roles) of a computer system for performing the subject matter described in the instant disclosure. The illustrated computer (602) is communicably coupled with a network (630). In some implementations, one or more components of the computer (602) may be configured to operate within environments, including cloud-computing-based, local, global, or other environment (or a combination of environments).

At a high level, the computer (602) is an electronic computing device operable to receive, transmit, process, store, or manage data and information associated with the described subject matter. According to some implementations, the computer (602) may also include or be communicably coupled with an application server, e-mail server, web server, caching server, streaming data server, business intelligence (BI) server, or other server (or a combination of servers).

The computer (602) can receive requests over network (630) from a client application (for example, executing on another computer (602)) and responding to the received requests by processing the said requests in an appropriate software application. In addition, requests may also be sent to the computer (602) from internal users (for example, from a command console or by other appropriate access method), external or third-parties, other automated applications, as well as any other appropriate entities, individuals, systems, or computers.

Each of the components of the computer (602) can communicate using a system bus (603). In some implementations, any or all of the components of the computer (602), both hardware or software (or a combination of hardware and software), may interface with each other or the interface (604) (or a combination of both) over the system bus (603) using an application programming interface (API) (612) or a service layer (613) (or a combination of the API (612) and service layer (613). The API (612) may include specifications for routines, data structures, and object classes. The API (612) may be either computer-language independent or dependent and refer to a complete interface, a single function, or even a set of APIs. The service layer (613) provides software services to the computer (602) or other components (whether or not illustrated) that are communicably coupled to the computer (602). The functionality of the computer (602) may be accessible for all service consumers using this service layer. Software services, such as those provided by the service layer (613), provide reusable, defined business functionalities through a defined interface. For example, the interface may be software written in JAVA, C++, or other suitable language providing data in extensible markup language (XML) format or another suitable format. While illustrated as an integrated component of the computer (602), alternative implementations may illustrate the API (612) or the service layer (613) as stand-alone components in relation to other components of the computer (602) or other components (whether or not illustrated) that are communicably coupled to the computer (602). Moreover, any or all parts of the API (612) or the service layer (613) may be implemented as child or sub-modules of another software module, enterprise application, or hardware module without departing from the scope of this disclosure.

The computer (602) includes an interface (604). Although illustrated as a single interface (604) in FIG. 6, two or more interfaces (604) may be used according to particular needs, desires, or particular implementations of the computer (602). The interface (604) is used by the computer (602) for communicating with other systems in a distributed environment that are connected to the network (630). Generally, the interface (604 includes logic encoded in software or hardware (or a combination of software and hardware) and operable to communicate with the network (630). More specifically, the interface (604) may include software supporting one or more communication protocols associated with communications such that the network (630) or interface's hardware is operable to communicate physical signals within and outside of the illustrated computer (602).

The computer (602) includes at least one computer processor (605). Although illustrated as a single computer processor (605) in FIG. 6, two or more processors may be used according to particular needs, desires, or particular implementations of the computer (602). Generally, the computer processor (605) executes instructions and manipulates data to perform the operations of the computer (602) and any algorithms, methods, functions, processes, flows, and procedures as described in the instant disclosure.

The computer (602) also includes a memory (606) that holds data for the computer (602) or other components (or a combination of both) that can be connected to the network (630). For example, memory (606) can be a database storing data consistent with this disclosure. Although illustrated as a single memory (606) in FIG. 6, two or more memories may be used according to particular needs, desires, or particular implementations of the computer (602) and the described functionality. While memory (606) is illustrated as an integral component of the computer (602), in alternative implementations, memory (606) can be external to the computer (602).

The application (607) is an algorithmic software engine providing functionality according to particular needs, desires, or particular implementations of the computer (602), particularly with respect to functionality described in this disclosure. For example, application (607) can serve as one or more components, modules, applications, etc. Further, although illustrated as a single application (607), the application (607) may be implemented as multiple applications (607) on the computer (602). In addition, although illustrated as integral to the computer (602), in alternative implementations, the application (607) can be external to the computer (602).

There may be any number of computers (602) associated with, or external to, a computer system containing computer (602), wherein each computer (602) communicates over network (630). Further, the term "client," "user," and other appropriate terminology may be used interchangeably as appropriate without departing from the scope of this disclosure. Moreover, this disclosure contemplates that many users may use one computer (602), or that one user may use multiple computers (602).

Figure 7:
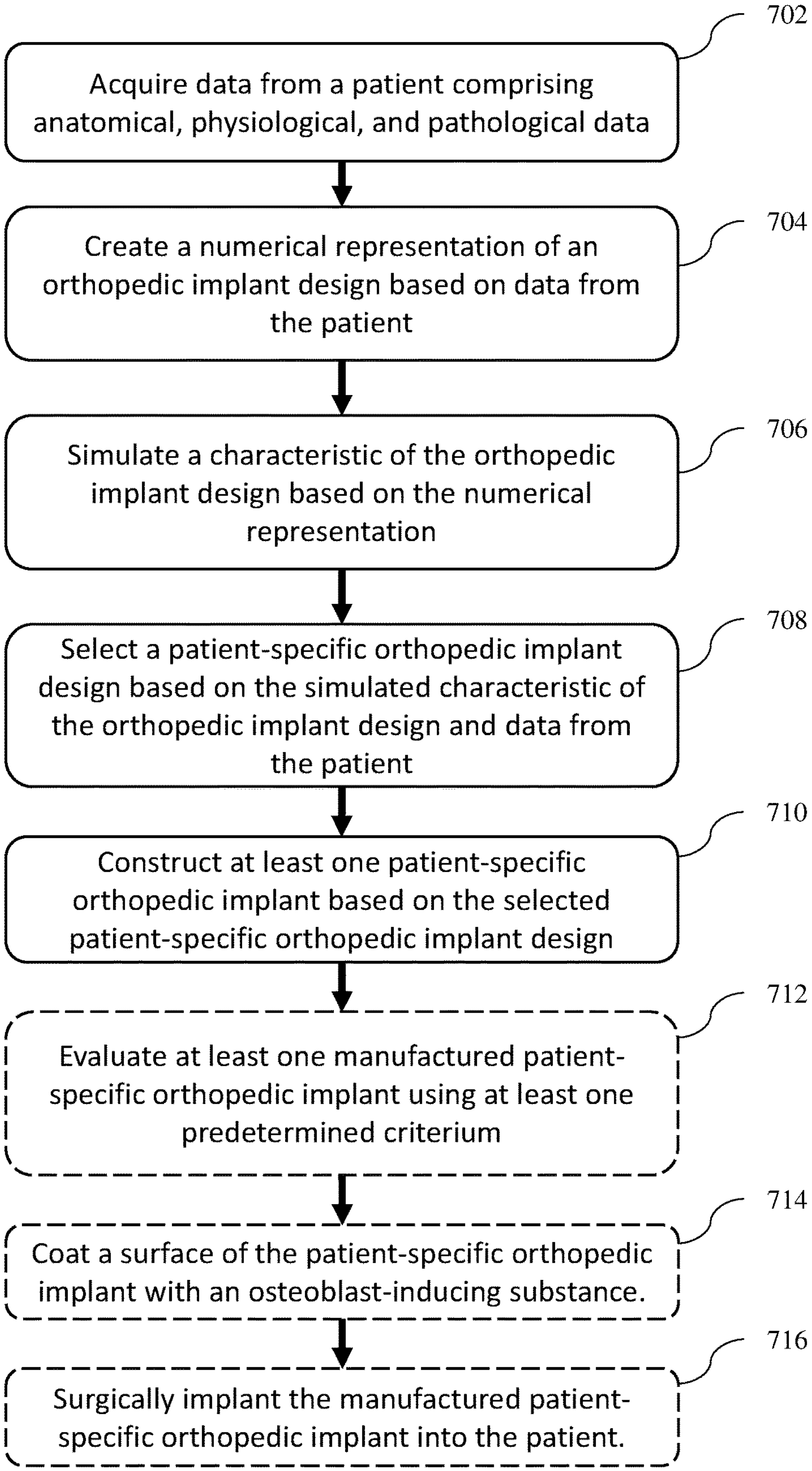
FIG. 7 shows a flowchart in accordance with one or more embodiments.

FIG. 7 shows a flowchart in accordance with one or more embodiments. In Step 702 patient data is acquired describing the anatomical, physiological, and pathological condition of the patient. The data may include data describing the healthy bone adjacent to the proposed orthopedic implant skeletal location. The data may be acquired by collecting one or more samples from healthy bone adjacent to the orthopedic implant site. Alternatively, one or more samples may be taken from an anatomically equivalent location. For example, if the proposed implant site is in a left femur then a sample may be taken from the right femur.

In Step 704 a numerical representation of an orthopedic implant design may be created based on the patient data. The representation may be stored in a computer memory in the form of computer readable data and instructions. The numerical representation may include a geometry of a lattice comprised of unit lattice cells. The numerical representation may further include a parameterization of the material from which the struts of the lattice are composed.

In Step 706, at least one characteristic of the orthopedic implant design may be simulated based on the numerical representation. The characteristic may include the density, porosity, permeability, at least one of elastic modulus, surface roughness, pore shape, resistance to wear, resistance to fatigue based failure, and osseointegration rate of the orthopedic implant. The simulation may be conducted using any one of DEM, FEM, DGM, FDM, FVM, LBM, SPH, and CA techniques.

In Step 708, a patient-specific orthopedic implant design may be selected based on the simulated characteristics of the orthopedic implant design and data from the patient. The selection may be performed to maximum the expected therapeutic lifetime of the implant by minimizing wear and fatigue-based failure, while facilitating speedy osseointegration and matching the mechanical properties of the orthopedic implant as closely as possible to those of the patient's healthy bone.

In Step 710, at least one patient-specific orthopedic implant, based on the selected patient-specific orthopedic implant design, may be manufactured. The manufacturing may be performed at least in part using an additive manufacturing technique. In particular, the additive manufacturing technique may comprise a powder bed fusion technique. In accordance with some embodiments, the additive manufacturing technique may form the orthopedic implant in its finished form. In other embodiments, the additive manufacturing technique may create an unfinished orthopedic implant that may subsequently be smoothed, polished, trimmed or combined with an additional component to create the finished orthopedic implant.

In accordance with one or more embodiments, in Step 712 at least one manufactured patient-specific orthopedic implant may be evaluated using at least one predetermined criterium. The evaluation may include the manufacturing of additional essentially similar copies of the manufactured patient-specific orthopedic implant to be used solely for evaluation. Evaluation may include determining if one or more characteristics, for example mechanical characteristics, of the orthopedic implant fall within a predetermined range. Evaluation may further include the redesign of the orthopedic implant using computational simulation if one or more of the characteristics of the current design fails to lie within its predetermined range. In accordance with other embodiments, Step 712 may be omitted.

In Step 714, in accordance with one or more embodiments, a surface of the patient-specific orthopedic implant may be coated with an osteoblast-inducing substance. The coating may include the impregnation of at least a layer of non-zero thickness beneath the surface of the orthopedic implant with an osteoblast-inducing substance. In accordance with other embodiments, Step 714 may be omitted.

Finally, in accordance with one or more embodiments, in Step 716 the manufactured patient-specific orthopedic implant may be surgically implanted into the patient for therapeutic purposes. In accordance with other embodiments, Step 716 may be omitted.

Figure 8:
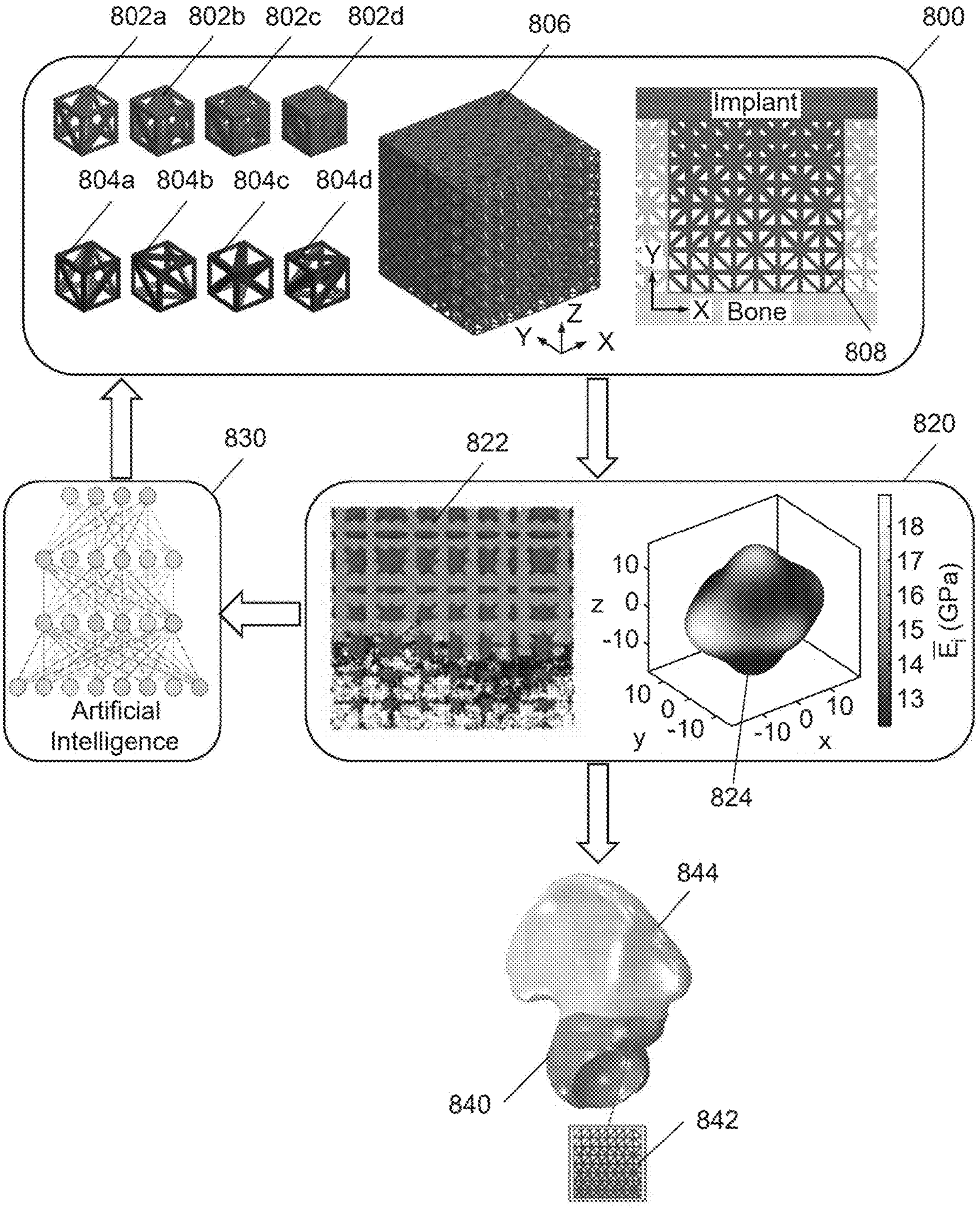
FIG. 8A-8C depict the structure, osseointegration, and elastic anisotropy for four meso-lattice cells in accordance with one or more embodiments.

FIGS. 8, 9A-9D, and 10 illustrate the steps of FIG. 7, in accordance with one or more embodiments. Chart 800 of FIG. 8 depicts some components of the numerical representation of the orthopedic implant. In this embodiment, four unit lattice cells (802*a*, 802*b*, 802*c*, and 802*d*) having varying strut thickness are used. The orientation of each unit lattice cells (802*a*, 802*b*, 802*c*, and 802*d*) may be selected from four different orientations (804*a*, 804*b*, 804*c*, and 804*d*) and combined into at least one meso-lattice cells structure (806). A plurality of meso-lattice cells (806) of at least one design may be attached to one another to form an architected material (808) from which the implant is to be formed.

Chart 820 of FIG. 8 depicts the simulation of the osseointegration characteristics (822) and the anisotropic elastic moduli (824) of the architected material (808). The simulation of the osseointegration characteristics is performed using an ABM technique. The ABM technique models the movement and growth of mesenchymal stem cells (MSCs), pre-osteoblast cells (OBp), and osteoblasts (OBa) using empirical rules to model cellular processes such as cell migration, cell proliferation, cell differentiation, and cell apoptosis.

The performance of the osseointegration characteristics (822) may be quantified using an osseointegration performance score. The similarity of the anisotropic elastic moduli (824) of the architected material and the anisotropic elastic moduli of the healthy bone of the patient was quantified using a stress-shielding prevention performance score. The components of the numerical representation of the architected material were optimized using artificial intelligence methods (830). When a design of the architected material that met the predetermined performance criteria was achieved the orthopedic implant (840) composed, at least in part, of the architected material (842) may be manufactured using an additive manufacturing method and implanted into the patient adjacent to the patients healthy bone (844).

Figure 9A:
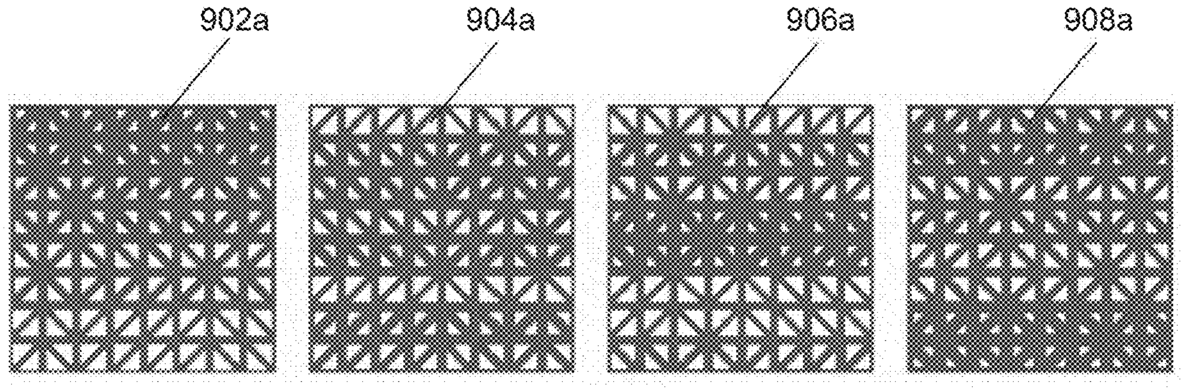
FIG. 9 depicts the stress-shielding prevention performance score and the osseointegration score for a plurality of meso-lattice cell designs in accordance with one or more embodiments.
Figure 9B:
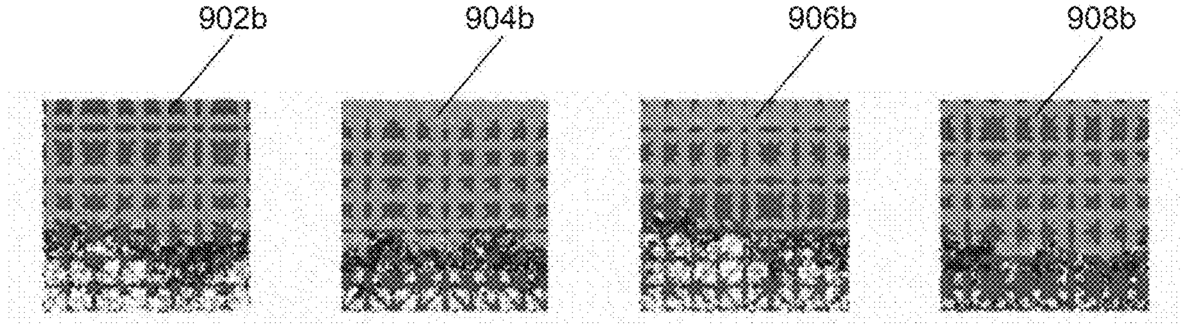
Figure 9C:
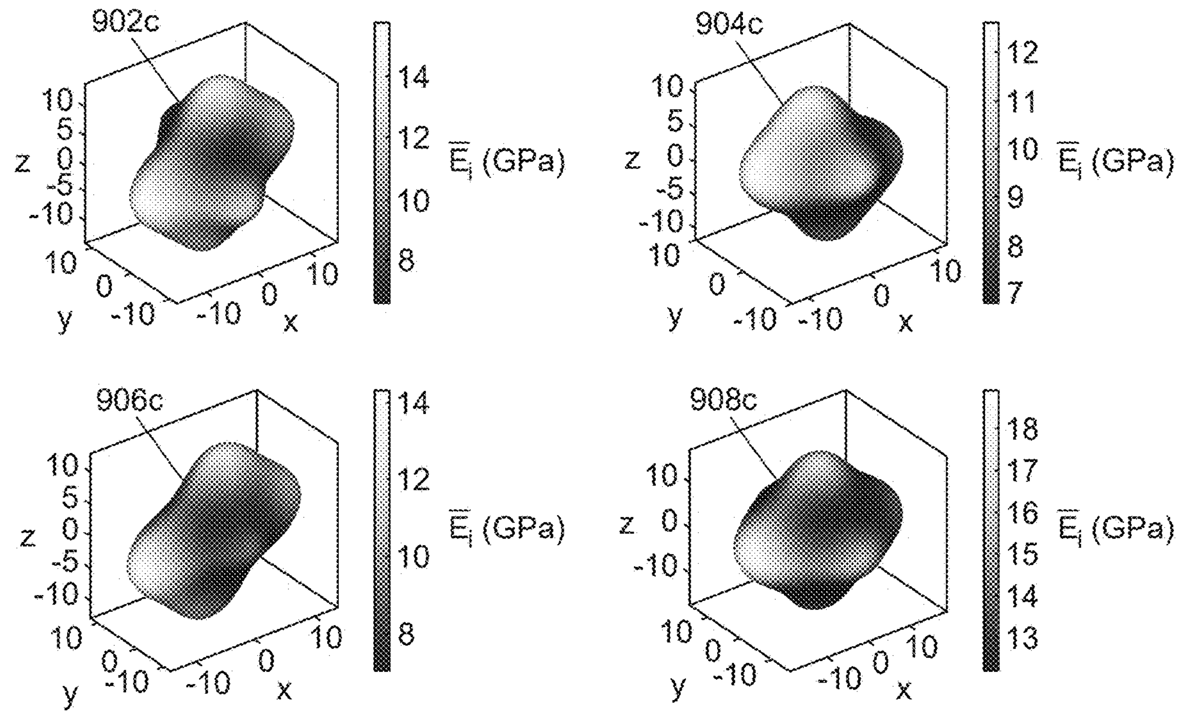

FIG. 9A depicts the structure of a selection of meso-lattice cells (902*a*, 904*a*, 906*a*, and 908*a*) for which a stress-shielding prevention performance score and an osseointegration score have been calculated. FIG. 9B shows the results of osseointegration modeling for each meso-lattice cell (902*b*, 904*b*, 906*b*, and 908*b*). FIG. 9C depicts the 3D anisotropic Young's modulus for each meso-lattice cell (902*c*, 904*c*, 906*c*, and 908*c*).

Meso-lattice cell (902*a*) shows fair osseointegration performance (902*b*) and fair stress-shielding prevention performance (902*c*), while meso-lattice cell (904*a*) shows poor osseointegration performance (904*b*) and poor stress-shielding prevention performance (904*c*). In contrast, meso-lattice cell (906*a*) shows good osseointegration performance (906*b*) but poor stress-shielding prevention performance (906*c*), and meso-lattice cell (908*a*) shows poor osseointegration performance (908*b*) but good stress-shielding prevention performance (908*c*).

Figure 10:
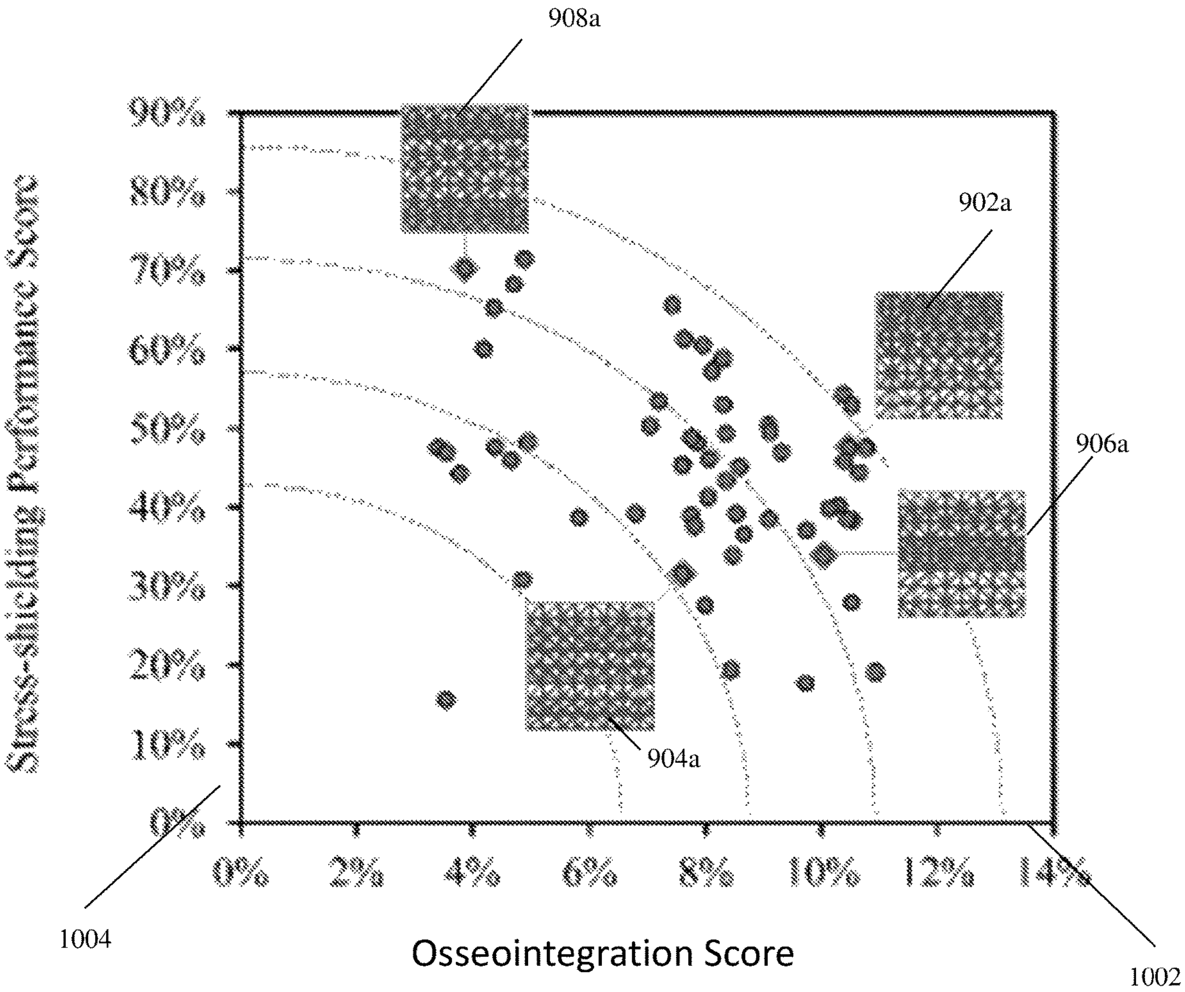

FIG. 10 displays the stress-shielding prevention performance score and an osseointegration score for 60 meso-lattice cells in a bivariate space of $PS_{BI}$, shown on the horizontal axis (1002) and $PS_{SS}$ shown on the vertical axis (1004). In FIG. 10 each meso-lattice cell design is represented by a dot on the 2D map. The further away the point representing a meso-lattice cell design is from the origin, the better its overall performance was. Points closer to the diagonal of the plane represented more balanced designs where osseointegration and stress-shielding prevention performed equally well. The stress-shielding performance score and osseointegration score of meso-lattice cells (902*c*, 904*c*, 906*c*, and 908*c*) are highlighted.

As described above, embodiments herein provide for patient-specific alternatives to traditional orthopedic implants, providing for custom made implants to suit the body size, age, and usage needs of every patient. Embodiments herein provide for computational modeling of implant designs, using multi-physics models to simulate the bone in-growth and agent-based models to optimize the implant geometry, advantageously resulting in improvement or optimization of the implant design, which is a function of porosity (forced o unwanted), permeability, pore shape, osteoblast inducing implant surface coating and surface roughness, to improve or maximize osseointegration. Further, embodiments herein may have lesser chance of rejection by the host body, as the implants are designed using agent-based modeling to simulate patient-specific bone growth simulations based on the data received, in some instances, from a few simple pathological tests. Overall, the multi-objective optimization of the porous implant microstructure according to embodiments herein allows for optimal lattice design for bone-implant interface, allowing for porous implants that mechanically stimulates the bone to avoid stress-shielding and is osseointegration friendly to allow maximum achievable bone ingrowth for improved long-term fixation.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

We claim:

1. A method for manufacturing a patient-specific orthopedic implant, the method comprising: creating, using a computer processor, a numerical representation of an orthopedic implant design based, at least in part, on patient data describing an anatomical, physiological and pathological condition of a patient; optimizing, using the computer processor, a simulated characteristic of the orthopedic implant design by varying a value of at least one parameter of the numerical representation and based on an osseointegration performance score, wherein the optimizing comprises finding an extremum of a cost function based, at least in part on the osseointegration performance score and a stress-shielding prevention performance score; selecting a patient-specific orthopedic implant design based, at least in part, on the simulated characteristic of the orthopedic implant design and the patient data; and manufacturing at least one patient-specific orthopedic implant based, at least in part, on the selected patient-specific orthopedic implant design.

2. The method of claim 1, further comprising evaluating the at least one manufactured patient-specific orthopedic implant using at least one predetermined performance criterion.

3. The method of claim 1, further comprising coating a surface of the at least one manufactured patient-specific orthopedic implant with an osteoblast-inducing substance.

4. The method of claim 1, wherein the optimizing the simulated characteristic of the orthopedic implant design comprises determining a variation with time of the simulated characteristic over a therapeutic lifetime of the orthopedic implant design.

5. The method of claim 1, wherein the simulated characteristic of the orthopedic implant design is selected from the group consisting of a density, a porosity, a permeability, a plurality of anisotropic elastic modulus, a surface roughness, a pore shape, a resistance to wear, a resistance to fatigue based failure, and osseointegration rate.

6. The method of claim 1, wherein the numerical representation comprises a geometry of an assembly of meso-lattice cells attached to one another, wherein each meso-lattice cell is formed from an assembly of unit lattice cells attached to one another.

7. The method of claim 1, wherein the patient data comprises a bone defect geometry and anisotropic elastic moduli of a bone.

8. The method of claim 1, wherein the numerical representation comprises:

a geometry of an exterior surface of the orthopedic implant design;

an elastic modulus of a material component of the orthopedic implant design; and a lattice structure of the material component.

9. The method of claim 1, wherein the manufacturing comprises an additive material manufacturing technique.

10. The method of claim 9, wherein the additive material is selected from the group comprising β tri-calcium phosphate, medical-grade titanium alloy, titanium-64, tantalum, cobalt-chrome, and polyether ether ketone.

11. The method of claim 1, wherein optimizing the simulated characteristic of the orthopedic implant design comprises applying at least one method selected from the group consisting of a discrete element method, a computational fluid dynamics method, a computational solid mechanics method, a finite element method, a computational bone mechanics method, a cellular automata method, and an agent-based modeling technique.

12. The method of claim 11, wherein optimizing the simulated characteristic of the orthopedic implant design further comprises applying artificial intelligence techniques.

13. A patient-specific orthopedic implant formed by the method of claim 1.

14. A system for creating a patient-specific orthopedic implant, comprising: a computer processor configured to: create a numerical representation of an orthopedic implant design based, at least in part, on patient data describing an anatomical, physiological and pathological condition of a patient, optimize a simulated characteristic of the orthopedic implant design by varying a value of at least one parameter of the numerical representation and based on an osseointegration performance score, wherein the optimizing comprises finding an extremum of a cost function based, at least in part on the osseointegration performance score and a stress-shielding prevention performance score; select a patient-specific orthopedic implant design based, at least in part, on the simulated characteristic of the orthopedic implant design and the patient data; and an additive manufacturing machine, configured to manufacture at least one patient-specific orthopedic implant using an additive manufacturing material based, at least in part, on the selected patient-specific orthopedic implant design.

15. The system of claim 14, wherein the additive manufacturing machine is further configured to coat a surface of the at least one manufactured patient-specific orthopedic implant with an osteoblast-inducing substance.

16. The system of claim 14, wherein the numerical representation comprises a geometry of an assembly of meso-lattice cells attached to one another, wherein each meso-lattice cell is formed from an assembly of unit lattice cells attached to one another.

17. The system of claim 14, wherein the additive manufacturing material is selected from the group comprising β tri-calcium phosphate, medical-grade titanium alloy, titanium-64, tantalum, cobalt-chrome, and polyether ether ketone.

18. The system of claim 14, wherein optimizing the simulated characteristic of the orthopedic implant design further comprises applying artificial intelligence techniques.

* * * * *